United States Patent
Kuramochi

(10) Patent No.: US 9,198,810 B2
(45) Date of Patent: Dec. 1, 2015

(54) ABSORBENT ARTICLE

(71) Applicant: DAIO PAPER CORPORATION, Shikokuchuo-shi, Ehime (JP)

(72) Inventor: Mihoko Kuramochi, Sakura (JP)

(73) Assignee: DAIO PAPER CORPORATION, Ehime (JP)

(*) Notice: Subject to any disclaimer, the term of this patent is extended or adjusted under 35 U.S.C. 154(b) by 0 days.

(21) Appl. No.: 14/355,313

(22) PCT Filed: Oct. 29, 2012

(86) PCT No.: PCT/JP2012/077861
§ 371 (c)(1),
(2) Date: Apr. 30, 2014

(87) PCT Pub. No.: WO2013/065630
PCT Pub. Date: May 10, 2013

(65) Prior Publication Data
US 2014/0288520 A1 Sep. 25, 2014

(30) Foreign Application Priority Data

Oct. 31, 2011 (JP) .................. 2011-238524

(51) Int. Cl.
*A61F 13/58* (2006.01)
*A61F 13/56* (2006.01)
*A61F 13/476* (2006.01)

(52) U.S. Cl.
CPC ........... *A61F 13/5616* (2013.01); *A61F 13/476* (2013.01)

(58) Field of Classification Search
CPC ............ A61F 13/47245; A61F 13/476; A61F 13/5616
See application file for complete search history.

(56) References Cited

U.S. PATENT DOCUMENTS

| | | | | |
|---|---|---|---|---|
| 5,344,416 A | * | 9/1994 | Niihara et al. | 604/385.04 |
| 6,458,112 B1 | * | 10/2002 | Marshall et al. | 604/385.04 |
| 2001/0027304 A1 | * | 10/2001 | Mayer | 604/385.14 |
| 2002/0052592 A1 | * | 5/2002 | Mills et al. | 604/385.04 |
| 2002/0058919 A1 | * | 5/2002 | Hamilton et al. | 604/385.05 |
| 2003/0139723 A1 | * | 7/2003 | Drevik | 604/385.04 |
| 2004/0068247 A1 | * | 4/2004 | Connor | 604/387 |
| 2006/0149201 A1 | * | 7/2006 | Sato et al. | 604/385.02 |
| 2006/0149202 A1 | * | 7/2006 | Cardin et al. | 604/385.04 |
| 2007/0100309 A1 | * | 5/2007 | Uda | 604/385.04 |
| 2010/0174258 A1 | | 7/2010 | Noda et al. | |
| 2010/0179494 A1 | | 7/2010 | Kuroda et al. | |
| 2010/0312215 A1 | | 12/2010 | Odoi | |
| 2012/0035567 A1 | * | 2/2012 | Kuroda et al. | 604/380 |

FOREIGN PATENT DOCUMENTS

| | | |
|---|---|---|
| JP | 3611761 | 1/2005 |
| JP | 2007-236649 | 9/2007 |

(Continued)

*Primary Examiner* — Susan Su
(74) *Attorney, Agent, or Firm* — Jordan and Hamburg LLP

(57) ABSTRACT

[Problem to be Solved]
To prevent curling of wing-shaped flaps to reduce an unnatural fit.
[Solution]
At least a part of the outline of a wing-shaped flap W has a wavy or curved line or wavy and curved lines in combination. A plurality of dot embosses 22 are provided on an outer edge along the outline of the wing-shaped flap W. Moreover, functional embosses 23 relatively larger in area than the dot embosses 22 are provided at the positions of convex portions 20 where the outline of the wing-shaped flap protrudes outward. Furthermore, central embosses 24 relatively larger in area than the dot embosses 22 are provided in a region where the dot emboss 22 is not provided, at the center of the wing-shaped flap.

8 Claims, 10 Drawing Sheets

(56) References Cited

FOREIGN PATENT DOCUMENTS

| | | | |
|---|---|---|---|
| JP | 2007236649 A | * | 9/2007 |
| JP | 2008-289658 | | 12/2008 |
| JP | 2009-125430 | | 6/2009 |
| JP | 2009-131442 | | 6/2009 |
| JP | 2010-125196 | | 6/2010 |
| JP | 2011-156239 | | 8/2011 |
| WO | WO-2008/146737 | | 12/2008 |
| WO | WO-2008/149771 | | 12/2008 |
| WO | WO-2011/096483 | | 2/2011 |

* cited by examiner (A)

(B)

(A)

(B)

ABSORBENT ARTICLE

TECHNICAL FIELD

The present invention relates to an absorbent article including wing-shaped flaps wrapped around the crotch of an undergarment when fixed to the undergarment.

BACKGROUND ART

For example, as shown in FIGS. 11 and 12, a conventional absorptive article N, e.g., a sanitary napkin, a pantiliner, a pad for vaginal discharge, and an incontinence pad is known. The absorptive article N contains an absorbing body 52 made of a cotton-state pulp between an impermeable back-surface sheet 50 such as a polyethylene sheet and a polyethylene laminate nonwoven cloth and a permeable front-surface sheet 51 such as a nonwoven cloth and a permeable plastic sheet.

In order to fix the absorbent article N of this type in an attached state, the absorbent article N, for example, includes one or more adhesive layer 53 formed on the skin non-contact surface (outer surface) of the absorbent article N, wing-shaped flaps W integrally formed on both sides of a napkin body in the longitudinal direction so as to extend to the outside, and adhesive layers 54 provided next to the impermeable back-surface sheet 50 on the surfaces (outer surfaces) of the wing-shaped flaps W.

When the absorbent article N is fixed to an undergarment 30, as illustrated in FIG. 13, the absorbent article N is fit to the crotch of the undergarment. The laterally extending wing-shaped flaps W are drawn from the undergarment. The wing-shaped flaps W are folded at folding lines RL and then are bonded to the outer surface of the crotch of the undergarment 30 so as to be wrapped around the crotch of the undergarment.

The outer edge of an absorbent article having the wing-shaped flaps W is provided with a sealing portion joining a front surface material and a back surface sheet. In Patent document 1, the sealing portion has irregularities that eliminate poor adhesion or damage to the sealing portion. Patent Document 1 discloses an absorbent article having concave or convex portions varying in pitch or area in the longitudinal or width direction of the absorbent article. Patent document 2 discloses an absorbent article including a sealing portion having a plurality of contact bonding portions for beeping the flexibility of the sealing portion. The contact bonding portions include a first contact bonding portion and a second contact bonding portion adjacent to the first contact bonding portion in a second direction. The first contact bonding portion and the second contact bonding portion are longer in a first direction than in the second direction.

CITATION LIST

Patent document 1: Japanese Patent No. 3611761
Patent document 2: Japanese Patent Laid-Open No. 2008-289658

SUMMARY OF INVENTION

Technical Problem

In recent years, the wing-shaped flaps W have had various stapes in plan view. In order to facilitate attachment or improve an exterior design, at least a part of the outline of a wing-shaped flap provided on a proposed absorbent article has a wavy or carved line or wavy and carved lines in combination. However, if the wing-shaped flaps having irregularities on the outline are provided with sealing portions described in Patent documents 1 and 2, portions protruding outward from the outline of the wing-shaped flap are insufficiently hard and thus may cause curling or twisting. This may lead to an unnatural fit.

A main object of the present invention is to provide an absorbent article that prevents curling of wing-shaped flaps so as to reduce an unnatural fit, the wing-shaped flap having a wavy or curved line or wavy and curved lines in combination at least on a part of the outline of the wing-shaped flap.

Solution to Problem

In order to solve the problem, an invention according to a first aspect is an absorbent article including wing-shaped flaps formed on respective sides of a body containing an absorbing body between a permeable front-surface sheet and an impermeable back-surface sheet, the wing-shaped flaps being fixed so as to wrap around a crotch of an undergarment upon attachment, wherein at least a part of the outline of the wing-shaped flap has a wavy or curved line or wavy and curved lines in combination, a plurality of dot embosses are provided on an outer edge along the outline of the wing-shaped flap, and functional embosses relatively larger in area than the dot embosses are provided at the positions of convex portions where the outline of the wing-shaped flap protrudes outward.

According to the invention of the first aspect, at least a pare of the outline of the wing-shaped flap has a wavy or curved line or wavy and curved lines in combination, a plurality of dot embosses are provided on the outer edge along the outline of the wing-shaped flap, and the functional embosses relatively larger in area than the dot embosses are provided at the positions of convex portions where the outline of the wing-shaped flap protrudes outward. Thus, the dot embosses can provide hardness along the outer edge of the wing-shaped flap, the hardness of the convex portions can be increased by the functional embosses provided at the positions of the convex portions protruding outward, and curling or twisting is prevented on the convex portions when the wing-shaped flap is folded during attachment, thereby reducing an unnatural fit.

An invention according to a second aspect is the absorbent article according to the first aspect, wherein the functional emboss is 10 to 25 times larger in area than the dot emboss.

The invention according to the second aspect specifies a relative area ratio between the dot emboss and the functional emboss. The formation of the functional emboss 10 to 25 times larger in area than the dot emboss can prevent curling of the convex portions of the wing-shaped flap with higher reliability.

An invention according to a third aspect is the absorbent article according to one of the first and second aspects, wherein the functional emboss is provided at a distance of 0 mm to 15 mm from the top of the convex portion where the outline of the wing-shaped flap protrudes outward.

In the invention according to the third aspect, in order to prevent curling of the wing-shaped flap, the functional emboss is located at a distance of 0 mm no 15 mm from the top of the convex portion where the outline of the wing-shaped flap protrudes outward.

An invention according to a fourth aspect is the absorbent article according to one of the first to third aspects, wherein the functional emboss is to road to the outside of a virtual line connecting concave portions on the outline of the wing-shaped flap.

In the invention according to the fourth aspect, the functional emboss is formed to the outside of the virtual line connecting the concave portions of the outline of the wing-shaped flap, thereby preventing curling of the convex portions with higher reliability.

An invention according to a fifth aspect is the absorbent article according to one of the first to fourth aspects, wherein at the position of the concave portion where the outline of the wing-shaped flap is recessed inward, the dot emboss is disposed along the concave portion and is concentrically provided substantially from the center position of a curve forming the concave portion.

In the invention according to the fifth aspect, at the position of the concave portion where the outline of the wing-shaped flap is recessed inward, the dot emboss is disposed along the concave portion and is concentrically provided substantially from the center position of the carve forming the concave portion. This enhances irregularities on the wing-shaped flaps so as to improve the design. The irregularities on the outline further improve ease of attachment.

An invention according to a sixth aspect is the absorbent article according to one of the first to fifth aspects, wherein a central emboss relatively larger in area than the dot emboss is provided in a region where the dot emboss is not provided, at the center of the wing-shaped flap.

In the invention according to the sixth aspect, the central emboss relatively larger in area than the dot emboss is provided in the region where the dot emboss is not provided, at the center of the wing-shaped flap. This increases hardness also at the center of the wine-shaped flap, facilitating attachment.

An invention according to a seventh aspect is the absorbent article according to the sixth aspect, wherein the central emboss is provided such that a straight line connecting central embosses close to the outline of the wing-shaped flap and a virtual line linearized from the outline are extended substantially in parallel with each other.

In the invention according to the seventh aspect, the central emboss is preferably provided such that the straight line connecting central embosses close to the outline of the wing-shaped flap and the virtual line linearized from the outline are extended substantially in parallel with each other.

Advantageous Effects of Invention

As has been specifically discussed, the present invention can provide an absorbent article that prevents curling of a wing-shaped flap and reduces an unnatural fit, the absorbent article including the wing-shaped flap such that at least a part of the outline or the wing-shaped flap has a wavy or curved line or wavy and curved lines in combination.

BRIEF DESCRIPTION OF THE DRAWINGS

FIG. 4(A) shows a conventional wing-shaped flap, and FIG. 4(B) shows the wing-shaped flap according to the present invention.

FIG. 5(A) shows the conventional wing-shaped flap, and FIG. 5(B) shows the wing-shaped flap according to the present invention.

DESCRIPTION OF EMBODIMENTS

Embodiments of the present invention will be specifically described below with reference to the accompanying drawings.

Sanitary Napkin 1

Figure 1:
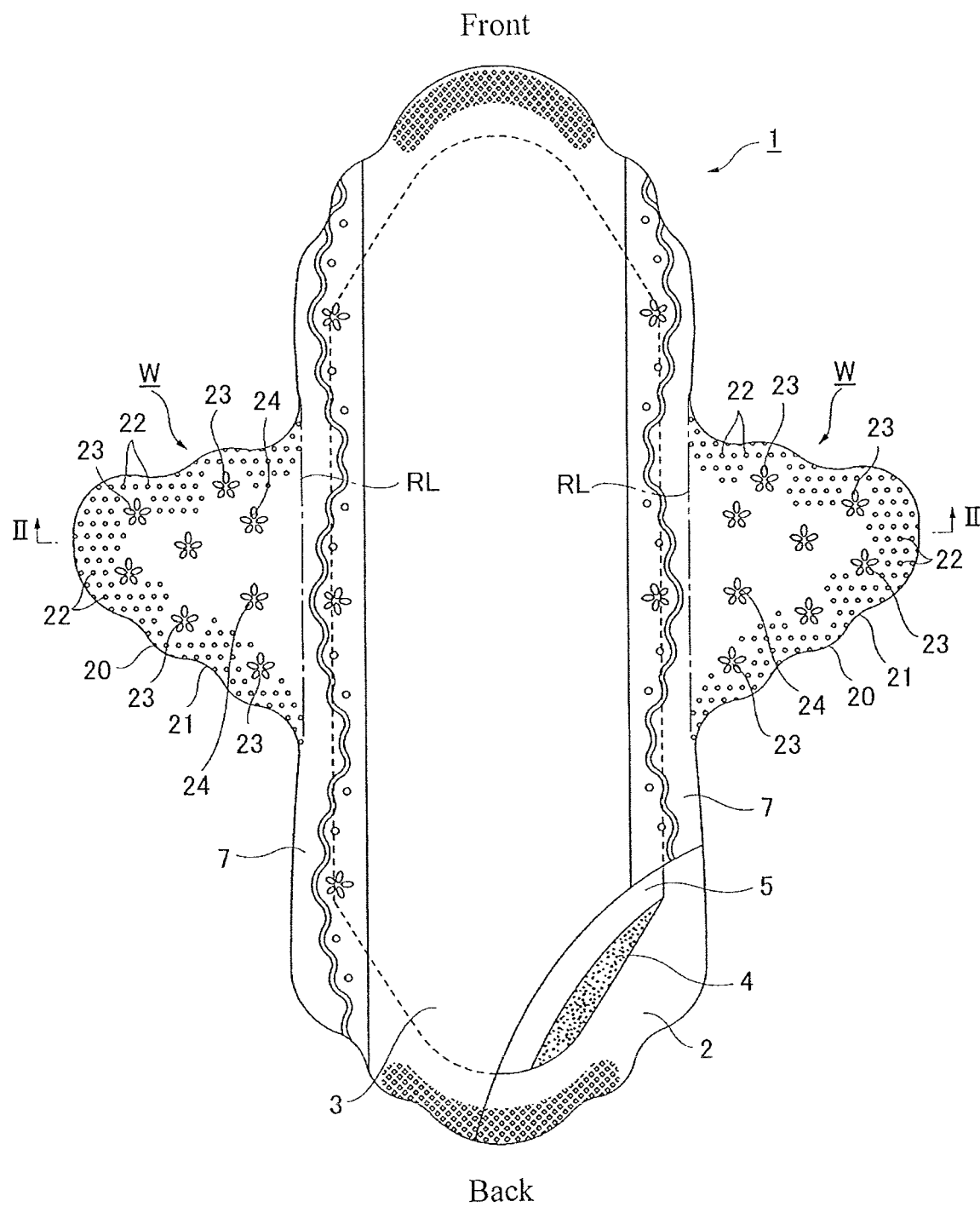
FIG. 1 is a partially cot development of a sanitary napkin 1 according to the present invention.
Figure 2:
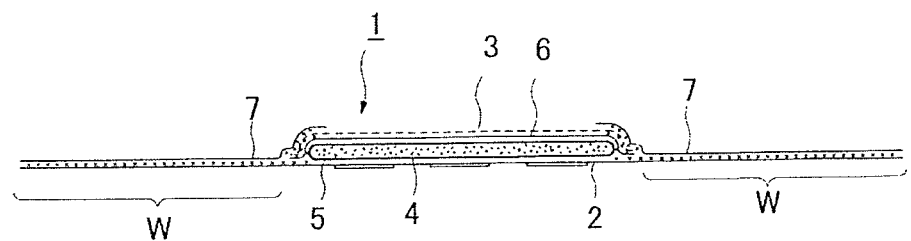
FIG. 2 is a cross-sectional view taken along line II-II of FIG. 1.

A sanitary napkin 1 according to the present invention includes, as illustrated in FIGS. 1 and 2, an impermeable back-surface sheet 2 composed of sheets such as a polyethylene sheet and a polypropylene sheet, a permeable front-surface sheet 3 which allows quick permeation of menstrual blood, vaginal discharge, and so on, an absorbing body 4 made of a cotton-state pulp or synthetic pulp interposed between the sheets 2 and 3, crepe paper 5 that surrounds the absorbing body 4 to keep the shape of the absorbing body 4 and improve dispersion, a second sheet 6 composed of a hydrophilic nonwoven cloth interposed between the permeable front-surface sheet 3 and the crepe paper 5, and side nonwoven cloths 7 formed in the longitudinal direction on both sides of the front surface. On the periphery of the absorbing body 4, the outer edges of the impermeable back-surface sheer 2 and the permeable front-surface sheet 3 on the upper and lower edges of the absorbing body 4 are joined with an adhesive such as hot-melt or by bonding means such as heat seal. Moreover, on the side edges of the absorbing body 4, the impermeable back-surface sheet 2 and the side nonwoven cloths 7, which laterally protrude out of the absorbing body 4, are joined with an adhesive such as hot-melt or by bonding means such as neat seal.

The structure of the sanitary napkin 1 will be further described below in detail.

A sheet material having at least water shielding performance, e.g., a sheet of olefin resins such as polyethylene and polypropylene is used for the impermeable back-surface sheet 2. Moreover, the sheer material may be a laminate nonwoven cloth including a nonwoven cloth laminated on a polyethylene sheet or the like, or a nonwoven cloth sheet containing a water-proof film to substantially ensure impermeability (in this case, the impermeable back-surface sheet is composed of a water-proof film and a nonwoven cloth). In recent years, the trend has shifted to sheets with moisture permeability in view of prevention of sticky feeling. The water-shielding/moisture permeable sheet material is a micro-porous sheet obtained by melting and kneading an inorganic filler in an olefin resin, e.g., polyethylene or polypropylene, molding a sheet, and then drawing the sheet in an uniaxial or biaxial direction.

A porous or non-porous nonwoven cloth or a porous plastic sheet is suitably used for the permeable front-surface sheet 3. Material fibers constituting the unwoven cloth may be synthetic fibers including olefins such as polyethylene and polypropylene, polyesters, and polyamide recycled, fibers such as rayon and cupra, and natural fibers such as cotton. Furthermore, a usable nonwoven cloth is obtained by appropriate processing methods such as spunrace method, spun-bond method, thermal bond method, melt-blown method, and needle punch method. Among these processing methods, the spunrace method is advantageous in its nigh flexibility and excellent drape property while the thermal bond method is advantageous in its bulkiness and softness. The permeable front-surface sheet 3 is desirably embossed in various ways from the top surface so as to increase retention of a body fluid and absorption efficiency, thereby preventing leakage in a lateral direction.

The absorbing body 4 interposed between the impermeable back-surface sheet 2 and the permeable front-surface sheet 3 is composed of, for example, fluff pulp and a water-absorbing polymer. The water-absorbing polymer is mixed in the pulp composing the absorbing body as, for example, granular powder. The pulp includes chemical pulp obtained from lumber, cellulose fibers such as molten pulp, and artificial cellulose fibers such as rayon and acetate. Softwood pulp with a fiber length longer than that of hardwood pulp is preferably used in terms of functions and price. The provision of the crepe paper 5 surrounding the absorbing body 4 in the present example locates the crepe paper 5 between the permeable front-surface sheet 3 and the absorbing body 4. The crepe paper 5 having high absorbency quickly diffuses a body fluid and prevents backflow of menstrual blood or the like.

The second sheet 6 composed of a hydrophilic nonwoven cloth interposed between the permeable front-surface sheet 3 and the crepe paper 5 contains synthetic fibers including olefins such as polyethylene and polypropylene, polyesters, and polyamide, recycled fibers such as rayon and cupra, and natural fibers such as cotton. A usable nonwoven cloth is obtained by appropriate processing methods such as spunrace method, spun-bond method, thermal bond method, melt-blown method, and needle punch method. In order to provide a hydrophilic property, synthetic fibers are made swollen or porous by using a method of polymerization through coexistence of a compound having a hydrophilic group such as an oxidized product of polyethylene glycol, for example, in a manufacture process of the synthetic fibers, and a method of precipitating a hydroxide of metal through treatment with metal salts such as stannic chloride and partial surface melting that forms a porous surface. The hydrophilic property can be obtained by applying a capillary phenomenon to the synthetic fibers.

The side nonwoven cloths 7 are provided on both sides of the front surface of this sanitary napkin 1 in the longitudinal direction substantially over the length of the napkin 1. The side nonwoven cloths 7 are partially extended in a lateral direction and form wing-shaped flaps W with a part of the impermeable back-surface sheet 2 that is similarly extended in the lateral direction. The wing-shaped flaps W will be specifically described later.

For the side nonwoven cloth 7, a water-repellent treated nonwoven cloth or hydrophilically treated nonwoven cloth can be used from the viewpoint of a function to be emphasized. For example, if an emphasis is to be placed on a function to prevent permeation of menstrual blood and vaginal discharge or the like or a function to improve a texture, a water-repellent treated nonwoven cloth coated with silicon, paraffin, alkyl chromic chloride water-repellent is desirably used. If an emphasis is placed on absorbency of menstrual blood or the like in the wing-shaped flaps W, a hydrophilically treated nonwoven cloth with a hydrophilic property is used. The hydrophilic property is provided by applying a capillary phenomenon. In the hydrophilically treated nonwoven cloth, the synthetic fibers are made swollen or porous by using a method of polymerization through coexistence of a compound having a hydrophilic group such as an oxidized product of polyethylene glycol, for example, in a manufacture process of the synthetic fibers, and a method of precipitating a hydroxide of metal through treatment with metal salts such as stannic chloride and partial melting that forms a porous surface.

Wing-Shaped Flap W

As shown in FIG. 1, on the sanitary napkin 1, at least a part of the outline of the wing-shaped flap W has irregularities, that is, a wavy or curved line or wavy and curved lines in combination. A plurality of dot embosses 22 are provided on an outer edge along the outline of the wing-shaped flap W. Moreover, functional embosses 23 relatively larger in area than the dot embosses 22 are provided at the positions of the convex portions where the outline of the wing-shaped flap W protrudes outward. Since the functional embosses 23 relatively larger in area than the dot embosses 22 are formed at the positions of the convex portions where the outline of the wing-shaped flap W protrudes outward, the functional embosses 23 on the convex portions of the wing-shaped flap W can have higher hardness than the dot embosses 22 simply formed uniformly along the outline of the wing-shaped flap W. This prevents curling or twisting of the wing-shaped flap W folded when the napkin is attached, thereby reducing an unnatural fit.

The provision of the dot embosses and the functional embosses provides the overall wing-shaped flaps with hardness so as to facilitate attachment to an undergarment, and enhances irregularities on the wing-shaped flaps so as to improve the design.

Figure 3:
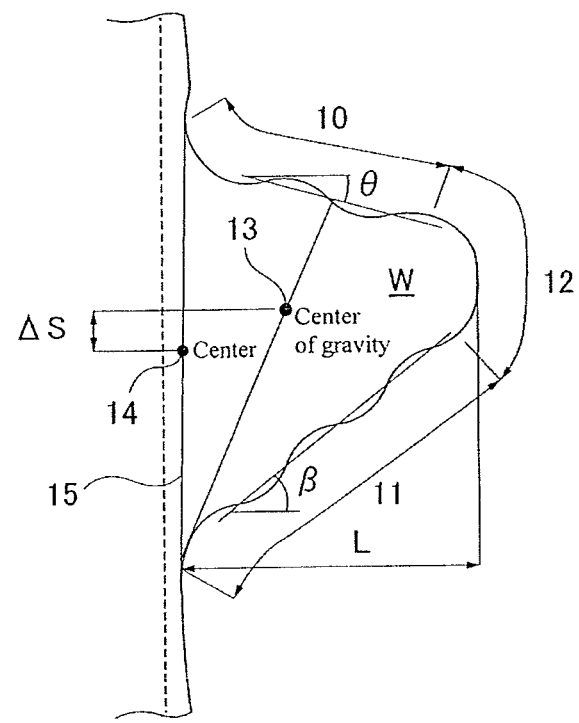
FIG. 3 is an enlarged plan view of a principal part of a wing-shaped flap.

Specifically, as shown in FIG. 3, the wing-shaped flap W has an outside shape including a front outline 10 extending outward from a body part, a rear outline 11 extending outward from the body part, and an end outline 12 connecting the front outline 10 and the rear outline 11. At least a part of the outlines has a wavy or curved line or wavy and curved lines in combination. Preferably, at least one of the front outline 10 and the rear outline 11 has a wavy or curved line or wavy and curved lines in combination.

The wing-shaped flap W of the sanitary napkin 1 is desirably shaped such that an angle $\beta$ formed by a width line of the sanitary napkin 1 and the rear outline 11 is larger than an angle $\theta$ formed by a width line of the sanitary napkin 1 and the front outline 10, and the center of gravity 13 of the wing-shaped flap W is shifted by $\Delta S$ from a center point 14 of a joining line 15 between the base and the body part of the wing-shaped flap W. These conditions are satisfied by a substantially triangular shape schematically shown in FIGS. 6(A) and 6(C) or a substantially uneven-leg trapezoid schematically shown in FIGS. 6(B) and 6(D). If the wing-shaped flap W is substantially triangular, the end outline 12 connecting the front outline 10 and the rear outline 11 may not be provided. Moreover, the front outline 10, the rear outline 11, and the end outline 12 do not always need to have a wavy or curved line or wavy and curved lines in combination and thus may partially have a straight line. If the front outline 10 and the rear outline 11 have a wavy or curved line or wavy and curved lines in combination, the angles θ and β may be formed by the center lines of the wavy or curved outline.

The angle θ formed by the width line of the sanitary napkin 1 and the front outline 10 is desirably about 0 to 20° while the angle β formed by the width line of the sanitary napkin 1 and the rear outline 11 is about 30 to 45°. In this case, an angle difference is desirably 15° or larger between the angle θ formed by the width line of the sanitary napkin 1 and the front outline 10 and the angle β formed by the width line of the sanitary napkin 1 and the rear outline 11. An angle difference of at least 15° can obtain a sufficient eccentricity ΔS. Thus, even if the wing-shaped flaps W are folded with a hand moving to the front, the napkin can be firmly attached in a normal state.

Fortunately, the wing-shaped flaps W having the outside shapes can be firmly folded a no bonded with ease at a normal folding position without causing bonding between adhesives or erroneous bonding. This point will be specifically described below in comparison with the conventional wing-shaped flap W (FIG. 10) shaped like an even-leg trapezoid.

Figure 4:
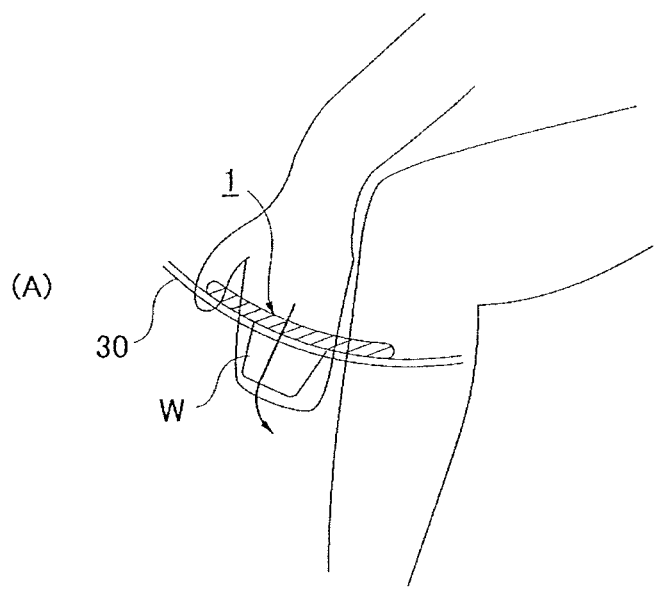
FIGS. 4(A) and 4(B) show an attachment process of the napkin.
Figure 4:
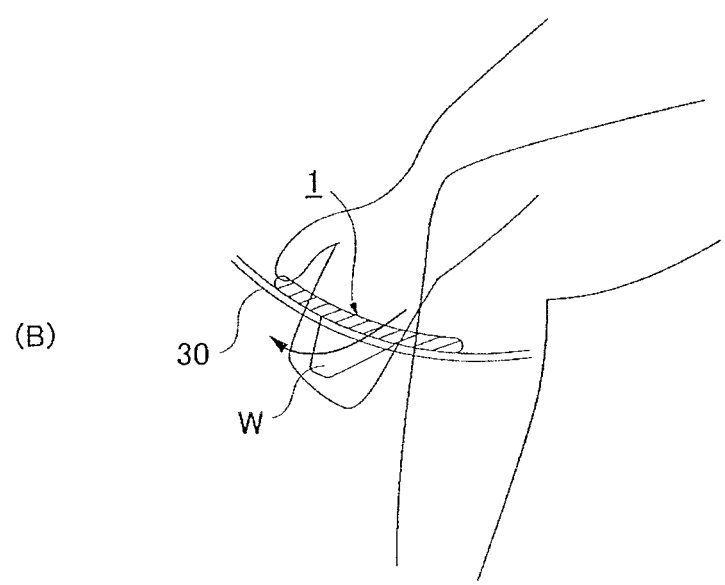

First, if a woman on a toilet bowl, etc. attaches the sanitary napkin 1 to an undergarment 30, as shown in FIG. 4, the napkin 1 is attached at the front of the body to the undergarment 30 having been pulled down by the woman.

In the case of the conventional wing-shaped flap W shaped like an even-leg trapezoid, as shown in FIG. 4(A), the napkin can be properly attached only by folding the wing-shaped flaps directly downward with a hand on both sides of the napkin. However, since the napkin is attached at the front of the body, a movement of the hand to the front (FIG. 4(B)) sometimes folds only a part of the wing-shaped flap. This joins adhesives so as to cause wrinkles or convex portions or folds the wing-shaped flap at an intermediate point so as to erroneously bond the wing-shaped flap to an adhesive layer. Moreover, the wing-shaped flap is sometimes folded with an inclined folding line. Hence, the present invention provides a wing shape firmly attachable in a normal state even if the wing-shaped flap is folded with a hand moving to the front as shown in FIG. 4(B).

Figure 5:
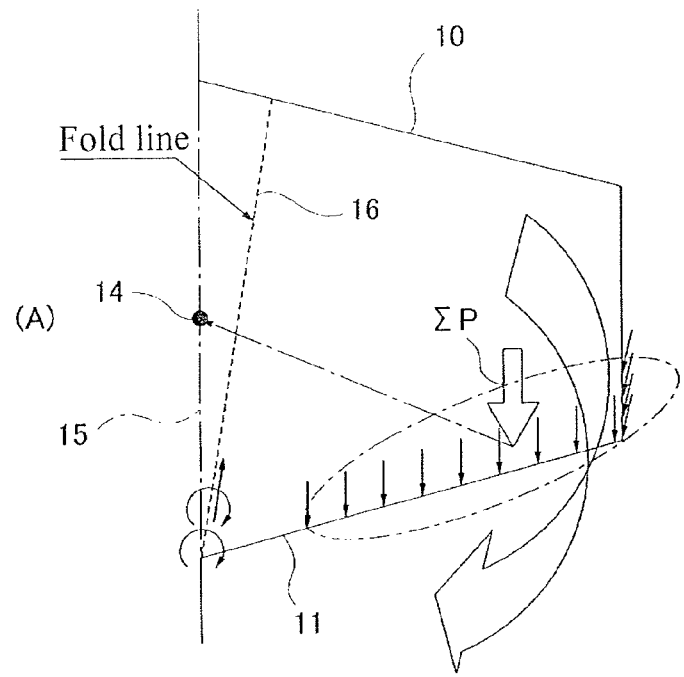
FIGS. 5(A) and 5(B) show a mechanism for applying a force when the wing-shaped flap is folded.
Figure 5:
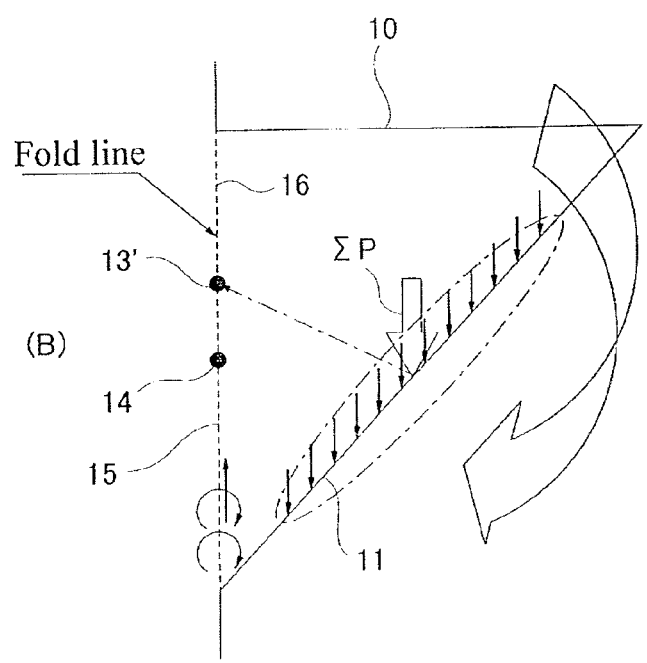

FIG. 5(A) shows an applied force mechanism when the conventional wing-shaped flap W with an even-leg trapezoidal shape is folded. If the wing-shaped flap is folded with a hand moving to the front, a load is applied downward from the rear outline to the end of the wing-shaped flap W. If the distributed load is assumed to be a concentrated load ΣP, the base point of a moment generated by the concentrated load ΣP is located at the center point 14 of the joining line 15 of the wing-shaped flap, twisting the folded wing-shaped flap W. Thus, a folding line 16 gradually extending from the proximal end of the rear outline 11 is inclined outward.

To address this problem, as shown in FIG. 5(B), the present invention applies a load downward to a center portion of the inclined rear outline 11. If the distributed load is assumed to be a concentrated load ΣP, the base point of a moment generated by the concentrated load ΣP is located at a center of gravity division point 13' (1:2 division point of the joining line 15) shifted to the front from the center point 14 of the joining line 15 of the wing-shaped flap. Since the folded wing-shaped flap W is hardly twisted, the folding line 16 gradually extending from the proximal end of the rear outline 11 coincides with the joining line 15, folding the wing-shaped flap W at a normal folding position.

The rear outline 11 of the wing-shaped flap W is largely inclined, folding the wing-shaped flap W precisely at a folding line RL without causing bonding between adhesives or erroneous bonding on the wing-shaped flap W.

The wing-shaped flap W preferably has a protrusion length L (FIG. 3) of at least 35 mm, preferably 40 to 50 mm. The wings preferably overlap each other along the crotch width of the undergarment 30 so as to firmly fix the wings to the undergarment. The proximal end of the wing-shaped flap W is preferably 80 mm or less in the longitudinal direction of the napkin, within the crotch of the undergarment.

Figure 6:
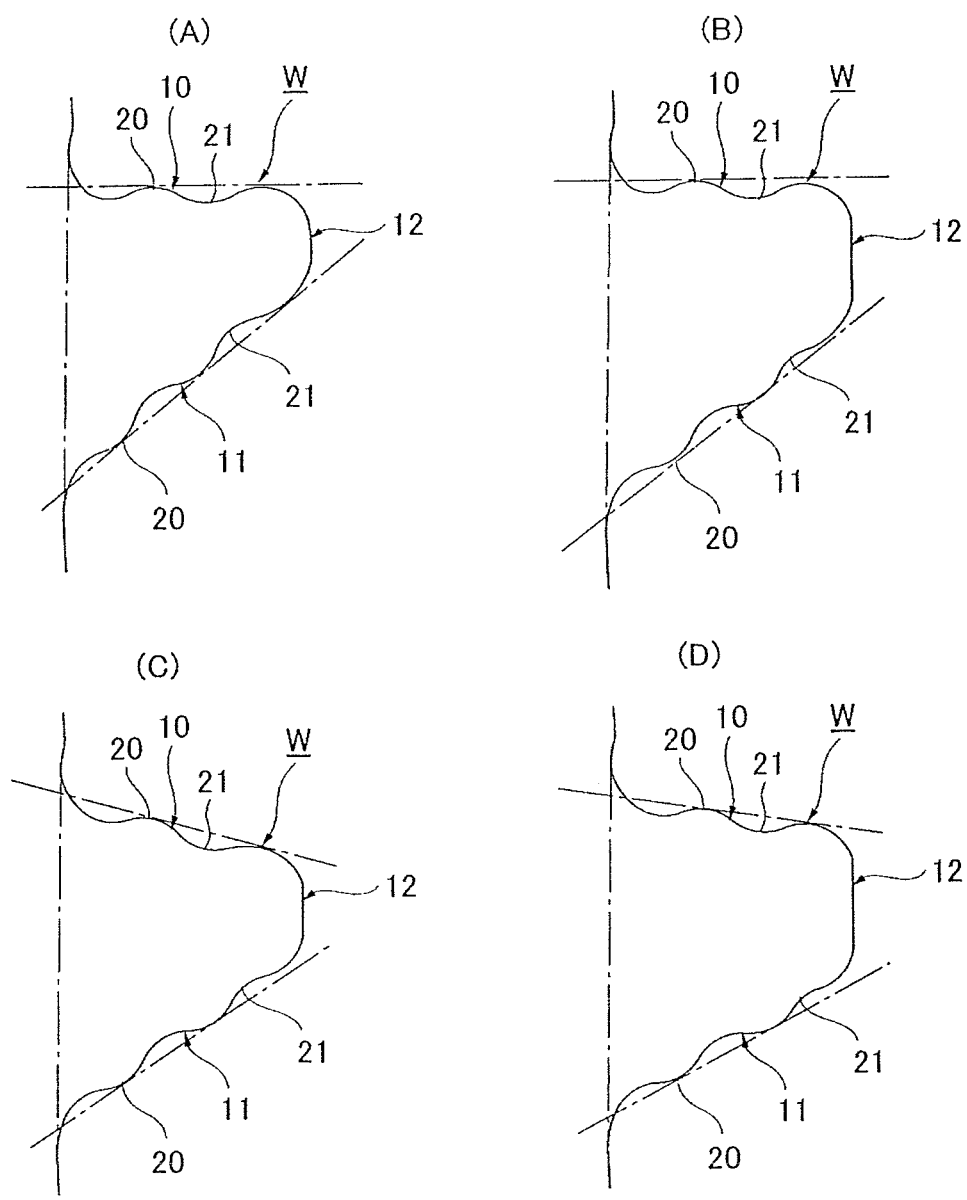
FIGS. 6(A) to 6(D) are schematic diagrams showing the shapes of the wing-shaped flap in plan view according to the present invention.

As shown in FIGS. 6(A) and 6(B), the outline of the wing-shaped flap W can be formed such that the front outline 10 substantially coincides with the width line. FIG. 6(A) shows the carved end outline 12 while FIG. 6(B) shows the end outline 12 having a linear portion. As shown in FIGS. 6(C) and 6(D), also in the case where the front outline 10 is inclined with respect to a width line, the end outline 12 can have a curved line (FIG. 6(C) or a linear line (FIG. 6(D)).

Figure 7:
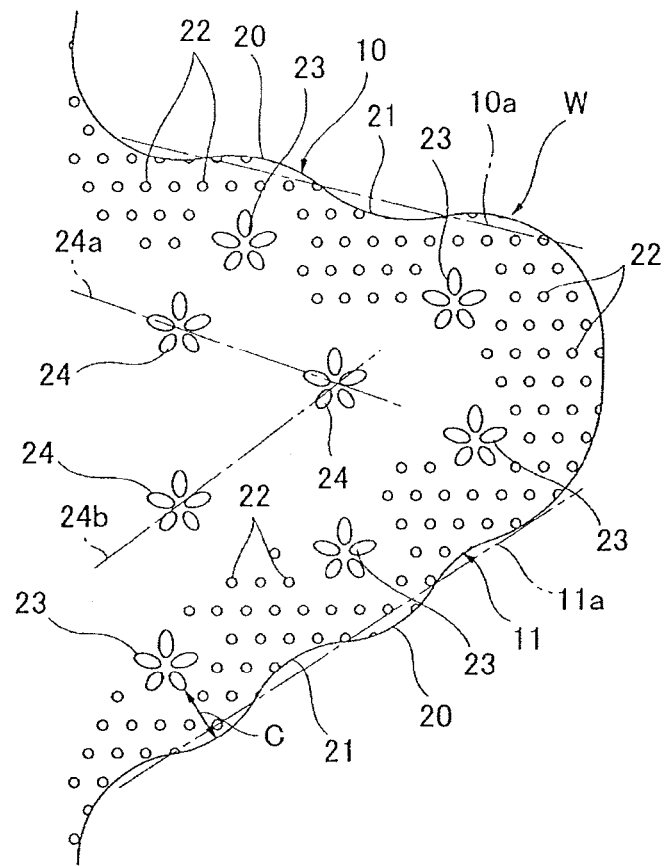
FIG. 7 is an enlarged plan view of the wing-shaped flap.

The embosses provided on the wing-shaped flap W will be specifically described below. As shown in FIG. 7, the dot embosses 22 with a predetermined width are formed in a predetermined pattern on an outer edge along the outline of the wing-shaped flap W. Specifically, the front outline 10 and the rear outline 11 each have a wavy or curved line or wavy or curved lines in combination. Furthermore, convex portions 20 and concave portions 21 are alternately formed. In this case, numbers of the dot embosses 22 are preferably formed in multiple rows on the outer edge along the outline according to the curved stapes of the convex portions 20 and the concave portions 21. Moreover, the dot embosses 22 are preferably formed over a range of 6 mm to 25 mm from the outline to the inside on the outer periphery of the wing-shaped flap W. The dot embosses 22 may be also formed inside the folding line RL of the wing-shaped flap W. However, as shown in FIG. 1, the dot embosses 22 are preferably formed only outside the folding line RL to facilitate bending of the wing-shaped flap W during attachment. The dot emboss 22 has an area of 0.2 $mm^2$ to 1.8 $mm^2$, preferably 0.5 $mm^2$ to 0.8 $mm^2$.

In the illustrated example, the dot embosses 22 are circular in plan view but may have any shapes, e.g., an oval, a triangle, a square, surd a scar. As shown in FIG. 7, the emboss pattern is preferably a staggered pattern extending along the longitudinal and width directions of the sanitary napkin 1 but the emboss pattern may be replaced with any patterns, e.g., a lattice pattern and a special layout pattern, which will be described laser. The embosses can be provided by thermo-compression bonding.

The functional embosses 23 are formed in an intermittent pattern according to the irregular shapes of the outline of the wing-shaped flap W. Specifically, if the outline of the wing-shaped flap W has the convex portions 20 and the concave portions 21 that are alternately formed, it is preferable to discretely form all the functional embosses 23 along the outline by forming the intermittent pattern for the positions of the convex portions 20 protruding outward from the outline of the wing-shaped flap W. The functional embosses 23 are relatively larger in area than the dot embosses 22. Specifically, the functional embosses 23 are 10 to 25 times, preferably 14 to 20 times larger in area than the dot embosses 22. It is preferable to form the functional embosses 23 separately from the dot embosses 22 without forcing the dot embosses 22 on the formation portions of the functional embosses 23.

The functional embosses 23 are formed at a predetermined length from the outline of the wing-shaped flap W. Specifically, as shown in FIG. 7, a separation width C from the top of the convex portion 20 protruding outward from the outline of the wing-shaped flap W to the functional emboss 23 is 0 mm to 15 mm. If the separation width C exceeds 15 mm, the effect of preventing curling of the convex portions 20 is considerably lessened.

Figure 8:
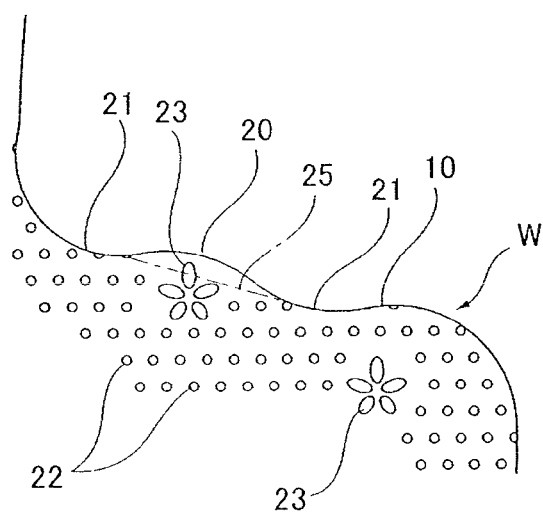
FIG. 8 is an enlarged plan view of the wing-shaped flap W according to another layout example of functional embosses 23.

As shown in FIG. 8, whole or a part of the functional embosses 23 are preferably formed to the outside of a virtual line 25 connecting the concave portions 21 adjacent to both sides of the convex portion 20 corresponding to the outline of the wing-shaped flap W. This can reliably prevent curling of the convex portion 20 of the wing-shaped flap W. The dot embosses 22 are formed as necessary. For example, if the functional embosses 23 are not formed to the outside of the virtual line 25 (FIG. 7), the dot embosses 22 are formed between the outline and the functional embosses 23. If the functional embosses 23 are formed to the outside of the virtual line 25 (FIG. 8), the dot embosses 22 are not formed between the outline and the functional embosses 23.

In the illustrated example, the functional emboss 23 in plan view has a plurality of oval portions radially disposed from lute center into a floral pattern. The functional emboss 23 may have any shapes including a heart, a rhombus, a star, a ribbon, and a circle as long as the functional emboss 23 is relatively larger in area than the dot emboss 22. Moreover, the functional emboss 23 is not limited to a single shape but includes substantially a group of combined shapes as in the floral pattern of the illustrated example. If the functional emboss 23 includes combined shapes, the total area of the combined shapes is relatively larger than the area of the dot embosses 22. The embosses can be provided by thermocompression bonding like the dot embosses 22.

As shown in FIG. 7, central embosses 24 relatively larger in area than the dot embosses 22 are provided in a region where the dot embosses 22 and the functional embosses 23 are not provided, at the center of the wing-shaped flap W. This increases hardness also at the center of the wing-shaped flap W, facilitating folding of the flap with ease of attachment. At this point, the central embosses 24 are preferably disposed such that a virtual line 10a linearized from the front outline 10 and a straight line 24a connecting the central embosses 24 close to the front outline 10 are substantially in parallel with each other at the front of the wing-shaped flap W while a virtual line 11a linearized from the rear outline 11 and a straight line 24b connecting the central embosses 24 close to the rear outline 11 are extended substantially in parallel with each other at the rear of the wing-shaped flap W. If the outline is formed by a straight line, the outline is the virtual line 10a or 11a that is linearized from the front outline 10 or the rear outline 11. If the outline is formed by wavy lines, the outline is any one of a virtual line (the example of FIG. 7) substantially passing through the center of the wavy line, a virtual line connecting the tops of the convex portions 20, and a virtual line connecting the tops of the concave portions 21. These straight lines are substantially disposed in parallel as long as the straight line 24a (24b) connecting the central embosses 24 is disposed in the range of ±10° relative to the virtual line 10a (11a). The central embosses 24 disposed thus obtain higher hardness than in a random layout, along the outline of the wing-shaped flap W, that is, in the protruding direction of the wing-shaped flap W. This facilitates attachment to an undergarment.

In the illustrated example, the two central embosses 24 are disposed on each of the front outline 10 and the rear outline 11 at the center of the wing-shaped flap W. Since the central emboss 24 located outside the other embosses is shared by the front outline 10 and the rear outline 11, the number of embosses is three in the overall wing-shaped flap W.

In the illustrated example, the central emboss 24 has a floral pattern like the functional emboss 23. The central emboss 24 may have any shapes including a heart, a rhombus, a star, a ribbon, and a circle as long as the central emboss 24 is relatively larger in area than the dot emboss 22. Moreover, the central emboss 24 may be identical in shape to the functional emboss 23 or may have a different shape from the functional emboss 23. The embosses can be provided by thermocompression bonding like the dot embosses 22.

Figure 9:
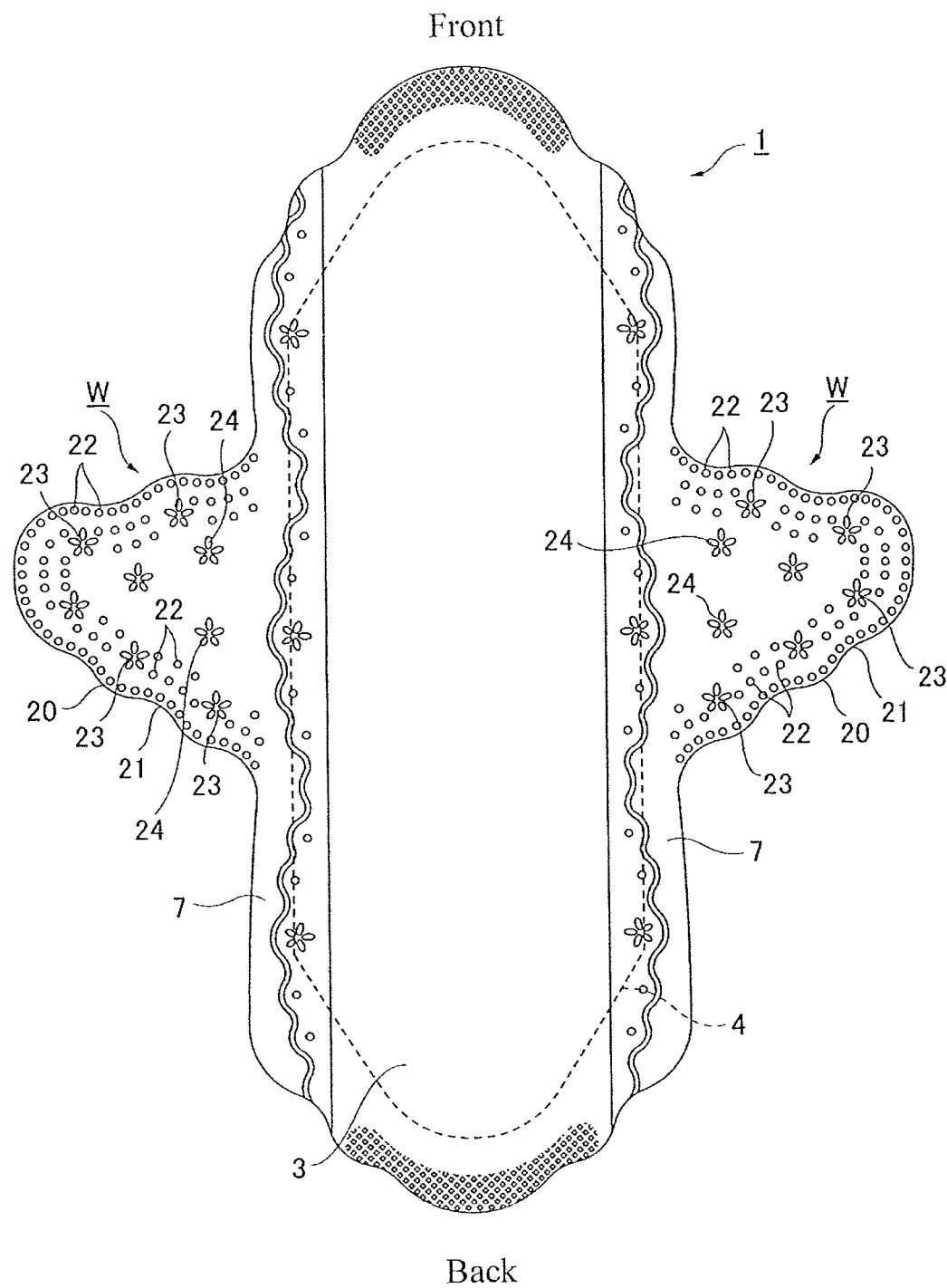
FIG. 9 is a development of a sanitary napkin 1 according to another embodiment.
Figure 10:
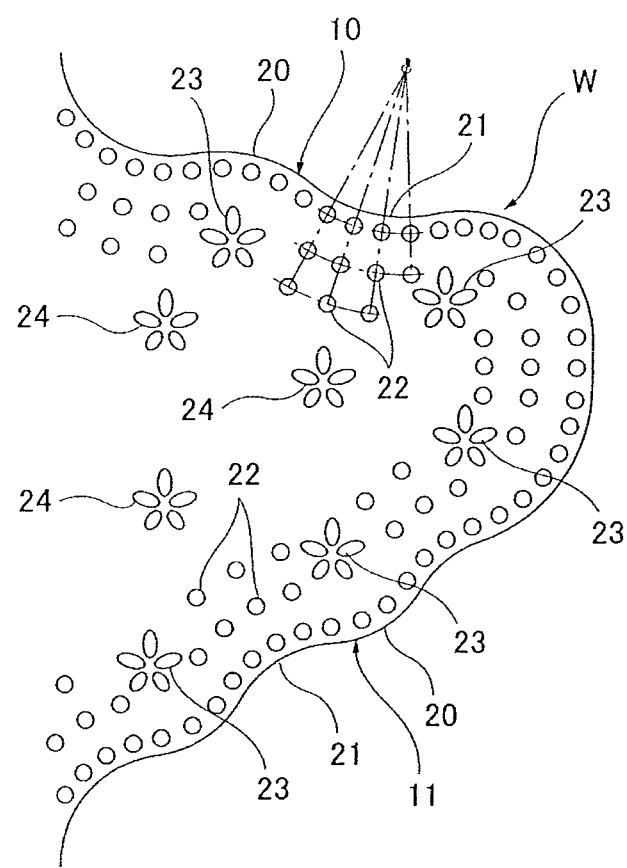
FIG. 10 is an enlarged plan view of the wing-shaped flap according to another embodiment.
Figure 11:
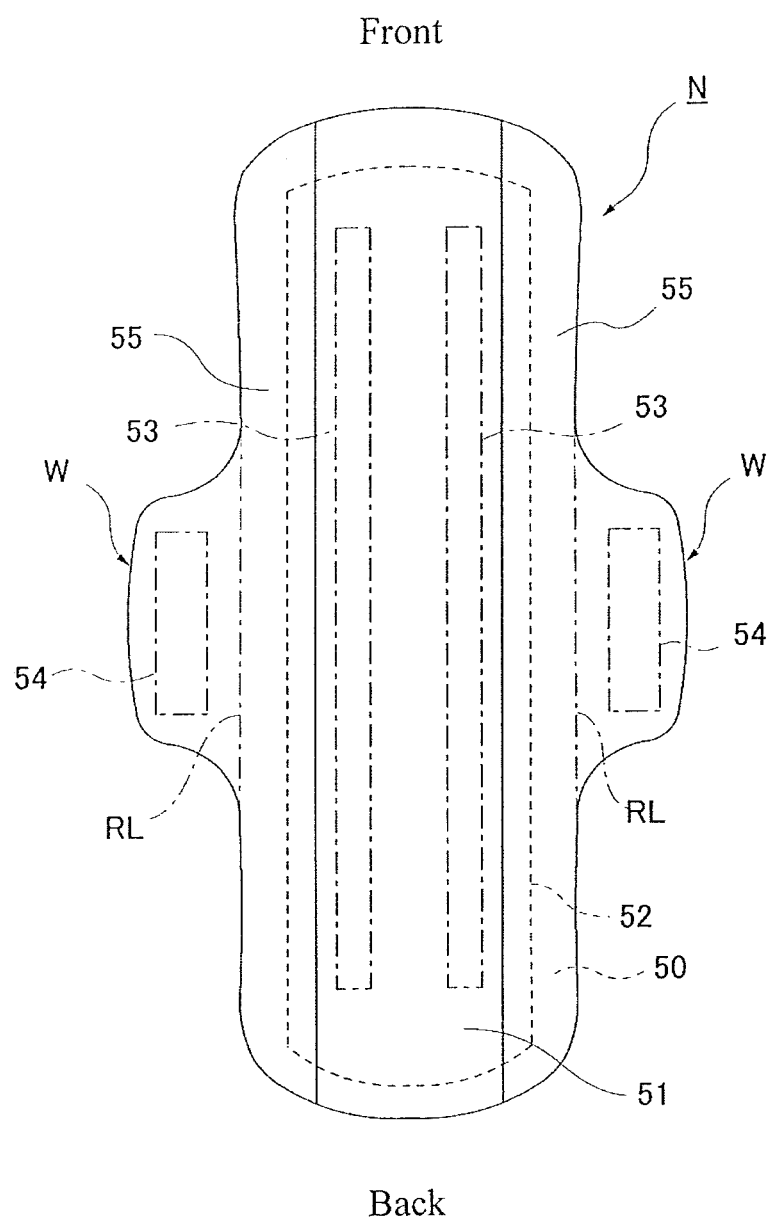
FIG. 11 is a development of a conventional sanitary napkin N.
Figure 12:
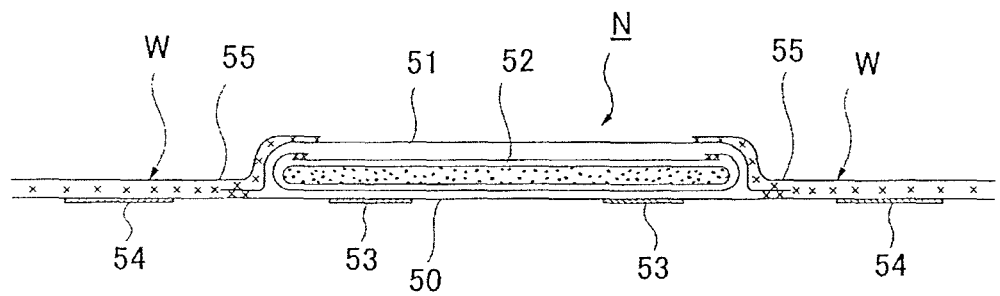
FIG. 12 is a cross-sectional view of the conventional sanitary napkin N of FIG. 11.
Figure 13:
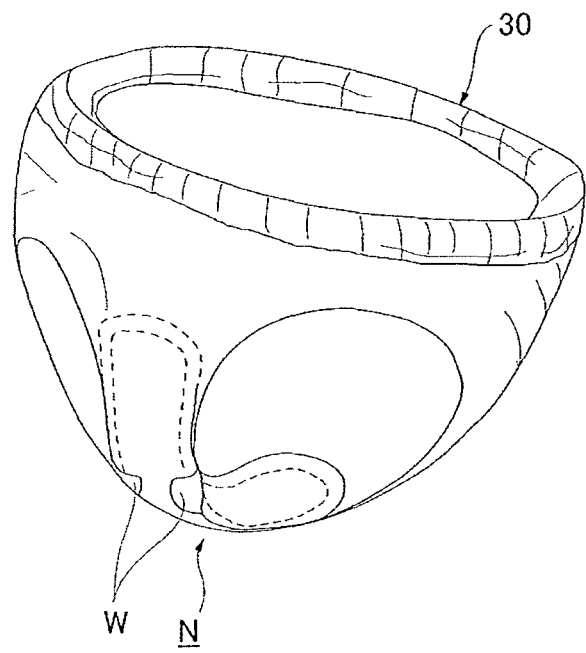
FIG. 13 shows a state of attachment of the conventional sanitary napkin N of FIG. 11.

Referring to FIGS. 9 and 10, a wing-shaped flap W according to another embodiment will be described below. The wing-shaped flap W according to the present embodiment has a different layout pattern of dot embosses 22 from the foregoing embodiments. Specifically, the dot embosses 22 are disposed along concave portions 21 of the outline of the wing-shaped flap W, at the positions of concave portions 21 where the outline of the wing-shaped flap W is recessed inward, and the dot embosses 22 are disposed substantially at regular angles on straight lines radially extended substantially from the center position of a curve forming the concave portion 21. The dot embosses 22 are concentrically disposed from the center position. The layout pattern of the dot embosses 22 enhances irregularities on the outline and improves the appearance. Moreover, irregularities on the outline further improve ease of attachment.

In the illustrated example, on the outer edge of the sanitary napkin 1 other than the wing-shaped flaps W, the front-surface material and the back-surface sheet 2 are joined with an adhesive such as hot-melt and embosses are provided by thermocompression bonding in predetermined regions on the front end and the rear end of the sanitary napkin 1.

Another Embodiment

A wing-fixing adhesive layer (not shown) formed, beside the impermeable back-surface sheet 2, on the surface of a wing-shaped flap W may be provided for the layout pattern of functional embosses 23 and/or central embosses 24. For example, the adhesive layers can be provided in any shapes such as a circle on the back sides of the functional embosses 23 (a surface near the impermeable back-surface sheet 2) so as to discretely provide the adhesive layers along the outline of the wing-shaped flap. Alternatively, the adhesive layer can be provided in a predetermined shape, e.g., a triangle connecting the three central embosses 24 on the back side of a region containing the central embosses. This can reinforce effects enhanced by the functional embosses 23 and/or the central embosses 24, further improving the attachment of the wing-shaped flap W.

REFERENCE SIGNS LIST 1 sanitary napkin
2 impermeable back-surface sheet
3 permeable front-surface sheet
4 absorbing body
5 crepe paper
6 second sheet
7 side nonwoven cloth
10 front outline
11 rear outline
12 end outline
20 convex portion
21 concave portion
22 dot emboss
23 functional emboss
24 central emboss
W wing-shaped flap

The invention claimed is:

1. An absorbent article comprising wing-shaped flaps formed on respective sides of a body portion containing an absorbing body between a permeable front-surface sheet and an impermeable back-surface sheet, the wing-shaped flaps being fixed so as to wrap around a crotch of an undergarment upon attachment, wherein each of the wing-shaped flaps has a front side contour line extending outwardly from the body portion and a rear side contour line extending outwardly from the body portion, and at least one of the front side and rear side contour lines is a wave shaped line where convex and concave portions are alternately formed, wherein a plurality of dot embosses are provided on an outer edge along an outline of the wing-shaped flap, and wherein functional embosses relatively larger in area than the dot embosses are provided at positions of convex portions where the outline of the wing-shaped flap protrudes outward.

2. The absorbent article according to claim 1, wherein each of the functional embosses is 10 to 25 times larger in area than the dot emboss.

3. The absorbent article according to claim 1, wherein each functional emboss is provided at a distance of 0 mm to 15 mm from a top of the convex portion where the outline of the wing-shaped flap protrudes outward.

4. The absorbent article according to claim 1, wherein each functional emboss is located in a vicinity of a corresponding one of the convex portions.

5. The absorbent article according to claim 1, wherein central embosses relatively larger in area than the dot emboss are provided in a region where the dot emboss is not provided, at the center of the wing-shaped flap.

6. The absorbent article according to claim 1, wherein said wave shaped line has multiple peaks and valleys.

7. An absorbent article comprising wing-shaped flaps formed on respective sides of a body containing an absorbing body between a permeable front-surface sheet and an impermeable back-surface sheet, the wing-shaped flaps being fixed so as to wrap around a crotch of an undergarment upon attachment, wherein at least a part of an outline of the wing-shaped flap has a wavy or curved line or wavy and curved lines in combination, a plurality of dot embosses are provided on an outer edge along the outline of the wing-shaped flap, and functional embosses relatively larger in area than the dot embosses are provided at positions of convex portions where the outline of the wing-shaped flap protrudes outward, and wherein at a position of a concave portion where the outline of the wing-shaped flap is recessed inward, the dot embosses are disposed along the concave portion and are concentrically provided substantially from a center position of a curve forming the concave portion.

8. An absorbent article comprising wing-shaped flaps formed on respective sides of a body containing an absorbing body between a permeable front-surface sheet and an impermeable back-surface sheet, the wing-shaped flaps being fixed so as to wrap around a crotch of an undergarment upon attachment, wherein at least a part of an outline of the wing-shaped flap has a wavy or curved line or wavy and curved lines in combination, a plurality of dot embosses are provided on an outer edge along the outline of the wing-shaped flap, and functional embosses relatively larger in area than the dot embosses are provided at positions of convex portions where the outline of the wing-shaped flap protrudes outward, wherein central embosses relatively larger in area than the dot emboss are provided in a region where the dot emboss is not provided, at the center of the wing-shaped flap, and wherein the central embosses are provided such that a straight line connecting the central embosses close to the outline of the wing-shaped flap and a virtual line linearized from the outline are extended substantially in parallel with each other.

\* \* \* \* \*